(12) United States Patent
Bodnar

(10) Patent No.: US 7,267,017 B1
(45) Date of Patent: Sep. 11, 2007

(54) METHOD TO TEST INDOOR AIR QUALITY

(76) Inventor: Michael D. Bodnar, 14300 202nd Ave., Elk River, MN (US) 55330

( * ) Notice: Subject to any disclaimer, the term of this patent is extended or adjusted under 35 U.S.C. 154(b) by 0 days.

(21) Appl. No.: 11/047,885

(22) Filed: Feb. 1, 2005

Related U.S. Application Data

(63) Continuation-in-part of application No. 10/714,705, filed on Nov. 17, 2003, now Pat. No. 6,898,960, which is a continuation-in-part of application No. 10/106,663, filed on Mar. 26, 2002, now Pat. No. 6,672,134.

(51) Int. Cl.
   *G01N 1/22* (2006.01)
(52) U.S. Cl. .................................... 73/863.23
(58) Field of Classification Search ............... 73/23.3, 73/23.2, 31.05, 31.06, 431, 866.5, 40, 38; 436/169, 170; 116/206; 356/437
See application file for complete search history.

(56) References Cited

U.S. PATENT DOCUMENTS

| | | | |
|---|---|---|---|
| 4,235,098 | A | 11/1980 | Tisch |
| 4,382,808 | A | 5/1983 | Van Wormer, Jr. et al. |
| 4,544,386 | A | 10/1985 | Trayford, III et al. |
| 4,649,760 | A | 3/1987 | Wedding |
| 4,963,167 | A | 10/1990 | Young |
| 5,012,681 | A | 5/1991 | Lentzen |
| 5,192,343 | A | 3/1993 | Henry |
| 5,205,155 | A | 4/1993 | Cooper |
| 5,500,369 | A | 3/1996 | Kiplinger |
| 5,593,470 | A | 1/1997 | Shagott et al. |
| 5,717,147 | A | 2/1998 | Basch et al. |
| 5,996,422 | A | 12/1999 | Buck et al. |
| 6,540,805 | B2 | 4/2003 | Ohno et al. |
| 6,613,130 | B2 | 9/2003 | Givargis |
| 6,672,134 | B2 * | 1/2004 | Bodnar ................. 73/28.01 |
| 6,898,960 | B1 * | 5/2005 | Bodnar ................. 73/28.04 |
| 6,993,985 | B2 * | 2/2006 | Srebro ................. 73/864.34 |
| 2002/0055176 | A1 * | 5/2002 | Ray ..................... 436/67 |

FOREIGN PATENT DOCUMENTS

| | | | |
|---|---|---|---|
| JP | 02144113 A | 6/1990 | ............ 73/863.23 |
| JP | 03221839 A | 9/1991 | ............ 73/28.01 |
| JP | 08313405 | * 11/1996 | |

OTHER PUBLICATIONS

OSHA ID-207, "Portland Cement (Total Dust) in Workplace Atmospheres", May 1991, available at http://www.osha.gov/dts/sltc/methods/inorganic/id207/id207.html.*
Division of Occupational Safety and Health P&P C-91, "Air Sampling Report", Aug. 1995, available at http://www.dir.ca.gov/DOSHPol/P&PC-91.htm.*
Paul A. Jensen, "Sampling and Characterization of Bioaerosols", Jan. 1998, NIOSH Manual of Analytical Methods.*
EMSL Analytical website, archived on Feb. 2001, available at http://web.archive.org/web/20010202060300/http://www.moldtestinglabs.com/.*
OSHA ID-160, "Asbestos in Air", Jul. 1998, available at http://www.osha.gov/dts/sltc/methods/inorganic/iid160/id160.html.*
OSHA regulation, 29 CFR 1910.1027 App F., Feb. 1996, pp. 1, 2, and 87.*
OSHA Regulation, Fed Reg 59:40964-41162, Aug. 1994, pp. 1 and 383-427.*

* cited by examiner

*Primary Examiner*—Michael Cygan
(74) *Attorney, Agent, or Firm*—Kinney & Lange, P.A.

(57) ABSTRACT

A method that allows an individual to personally test for contaminants in an air supply. The method consists of purchasing the test kit, placing the test kit on a device that produces air circulation and blowing air through the test kit. The test kit is then removed from the device, repackaged and sent to a laboratory for analysis. The air quality test kit comprises a test filter, a filter backing pad and a support, which together form a device that captures and retains particles carried in an airflow.

20 Claims, 3 Drawing Sheets

METHOD TO TEST INDOOR AIR QUALITY

CROSS-REFERENCE TO RELATED APPLICATION(S)

This is a Continuation-in-part of Ser. No. 10/714,705 filed Nov. 17, 2003 now U.S. Pat. No. 6,898,960 entitled "Indoor Air Quality Test Apparatus" which is a Continuation-in-part of Ser. No. 10/106,663, filed Mar. 26, 2002, now U.S. Pat. No. 6,672,134 B2 entitled "Indoor Air Quality Test Apparatus". Reference is hereby made to the following co-pending application, which was filed on even date with the present application, "Indoor Air Quality Test Apparatus", by Michael D. Bodnar.

BACKGROUND OF THE INVENTION

The present invention pertains to a method to test for contaminants in an indoor air supply. More particularly, the invention pertains to a method that allows an individual such as a homeowner to test for contaminants contained in an indoor air supply by utilizing devices that produce air circulation.

There is always a concern over whether contaminants exist in the air supply of an indoor room. Such concern arises because human or animal inhalation of contaminants may lead to respiratory infections and diseases. Additionally, fungus growing in a room can corrode metal surfaces, create an unappealing sight, become a serious fire hazard, and increase energy costs due to lower performance levels of air delivery systems. Contaminants that may be inhaled include fumes, fibers, allergens, fungi, bacteria and any other matter that poses a risk to indoor air quality.

The detection of contaminants in an indoor environment is crucial because most people cannot visually tell whether a room is contaminated. In addition, indoor rooms often do not have the appropriate ventilation to eliminate contaminants without the aide of experts. Therefore, various techniques have attempted to provide a means for detecting contaminants.

One technique is to call upon an industrial hygienist to visit a particular site and perform air monitoring tests utilizing special equipment. This technique, however, is labor intensive and often cost prohibitive, particularly for a residential homeowner.

A simple technique to detect the presence of contaminants in an indoor air supply is presently not available. The present invention is directed at a simple, inexpensive method to detect the presence of contaminants in an indoor air supply.

BRIEF SUMMARY OF THE INVENTION

The invention is a method that allows an individual to test for contaminants in an indoor air supply. The homeowner purchases the test kit which includes a test device having a test filter, a support and a filter backing pad. The test filter is made of a material that will capture and retain contaminants carried in the air. The support includes a central opening to which the test filter is attached. The homeowner then places the test device onto a device that produces air circulation. The air circulation device is then operated for a predetermined amount of time. The air circulation device is then turned off and the test device is removed from the air circulation device, repackaged and sent to a laboratory for analysis.

DETAILED DESCRIPTION

The present invention allows a homeowner to perform a test for airborne contaminants in a home or other building. In particular, the present invention is a versatile test kit that can be used with a variety of different devices that produce air circulation such as a heating and ventilation system, a box fan or a vacuum cleaner. The test kit allows a homeowner to obtain an air sample in a reasonable amount of time, which can then be mailed to a testing facility for analysis.

Figure 1:
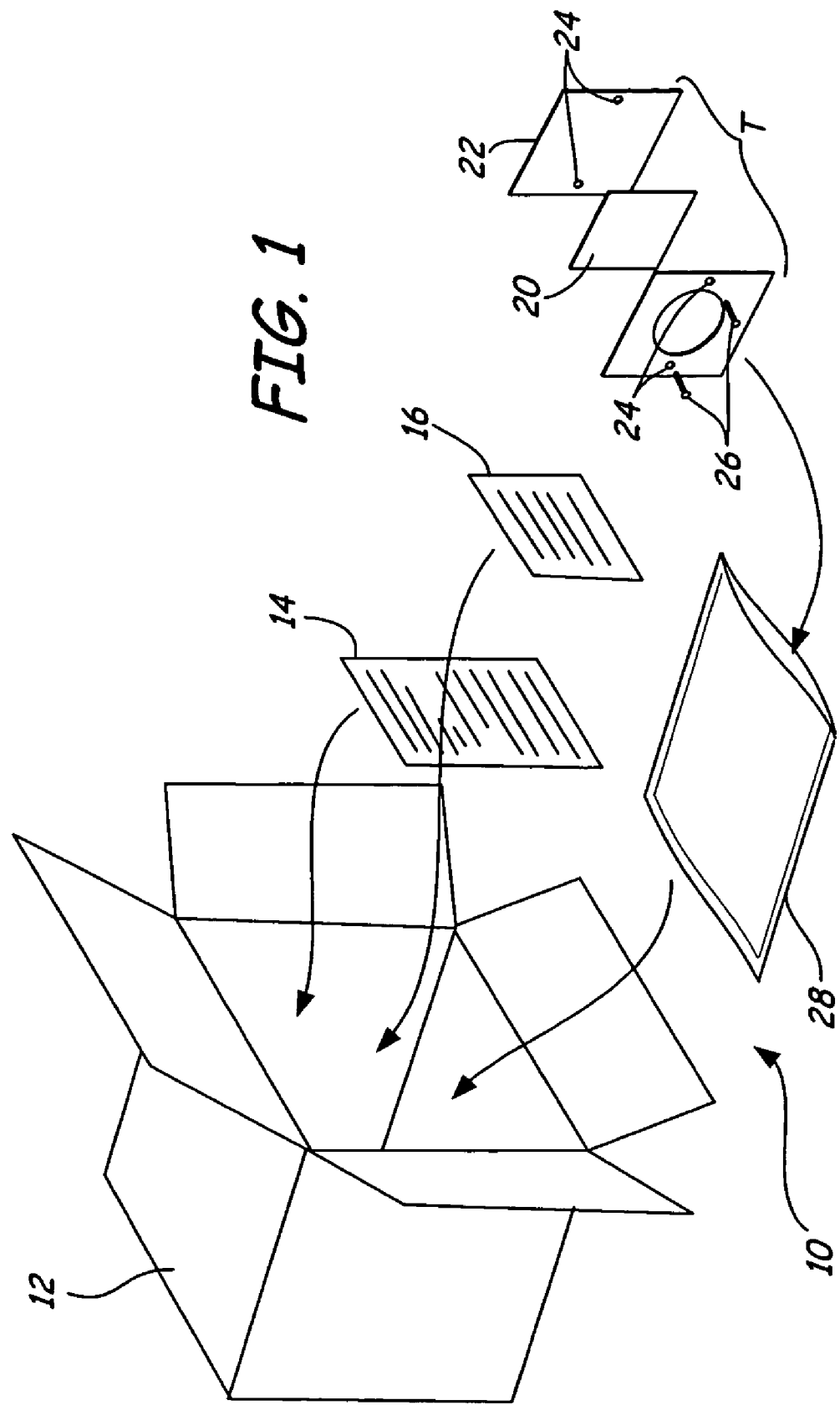
FIG. 1 is an exploded view of a test kit.

FIG. 1 shows the components comprising test kit 10. The test kit 10 includes a package 12, a set of instructions 14, an order form 16, a test device T (formed by a support 18, a test filter 20 and a filter backing pad 22), a pair of pin openings 24, a pair of pins 26 and a container 28. The test kit 10 is a pre-assembled kit stored within the package 12. The package 12 can be a box or any sort of container that can hold objects. The test kit 10 includes the set of instructions 14 and the order form 16. The instructions 14 explain how to use and install the test kit 10. The order form 16 is a series of questions that must be answered by the user of the test kit 10. The order form 16 assists the test facility in interpreting the contaminants collected by the test kit 10 to ensure more accurate results.

The test filter 20 is positioned such that it is sandwiched between the support 18 and the filter backing pad 22. The test filter 20 is mounted on the filter backing pad 22 such that the filter backing pad 22 provides support for the test filter 20. The test filter 20 is mounted on the filter backing pad 22 preferably by gluing the test filter 20 onto the filter backing pad 22. However, any adhesive or fastener may be used to mount the test filter 20 to the filter backing pad 22. The test filter 20 is preferably approximately a 50 square millimeter, mixed-cellulose ester.

The filter backing pad 22 is preferably made of a material with a low, restrictive airflow that is thick and sturdy enough to support the test filter 20 as well as withstand air pressure while the test device T is in use, such as paper or mesh screen. The filter backing pad 22 is preferably a square shape that has a width approximately 3.25 inches and a length approximately 3.25 inches. The filter backing pad 22 is preferably this shape and size so that the test device T can easily fit into a standard envelope for mailing to the testing facility for analysis. Additionally, this size allows a user to obtain a sample size small enough to be submitted through the mail but large enough for the testing facility to be able to perform an adequate analysis. However, the filter backing pad 22 can have a length less than approximately 3⅞ inches and a width less than approximately 3⅞ inches, a measurement not greater than the height of a standard envelope. The filter backing pad 22 should not be much smaller than the preferred size to ensure that an adequate sample size is obtained. Additionally, the test kit 10 is designed such that the pressure loss through the test filter 20 and the filter backing pad 22 approximately equals the pressure loss of air flowing through the support 18. This ensures that there is a uniform pressure across the support 18, the test filter 20 and the filter backing pad 22.

The support 18 is preferably a square shape with a width of approximately 3.25 inches and a length of approximately 3.25 inches. The support 18 is preferably this shape and size so that the test kit 10 can easily fit into a standard envelope for mailing to the testing facility for analysis. Additionally, this size allows a user to obtain a sample size small enough to be submitted through the mail but large enough for the testing facility to be able to perform an adequate analysis. However, the support 18 can have a length less than approximately 3⅞ inches and a width less than approximately 3⅞ inches, a measurement not greater than the height of a standard envelope. The support 18 should not be much smaller than the preferred size to ensure that an adequate sample size may be obtained. The support 18 and the filter backing pad 22 should have the same shape and size to permit easy mailing of the test kit 10 to the testing facility.

The support 18 is preferably made of a porous cardboard material that supports the test filter 20 and the filter backing pad 22. The support 18 includes a central opening to which the test filter 20 is attached. The test filter 20 is attached to the support 18 preferably by gluing the test filter 20 to the support 18, however, any adhesive or fastener may be used to attach the test filter 20 to the support 18. The central opening of the support 18 preferably has a circular shape with a diameter of approximately 2 inches. The central opening of the support 18 has this shape and size so that the test kit 10 can be used with a vacuum cleaner attachment hose. The shape and size of the central opening of the support 18 is consistent with the shape and size of the vacuum cleaner attachment hose. Additionally, the central opening of the support 18 has this shape and size to ensure that an adequate sample size is obtained.

A pair of pin openings 24 extend through the support 18 and the filter backing pad 22. The pin openings 24 provide a place to insert the pair of pins 26. The pair of pins 26 can be used to help fasten the test device T. Although a pair of pin openings 24 are shown, the test kit 10 can be made with a single pin opening or with a plurality of pin openings.

The container 28 is used to cover the test filter 20 when the test device T is not in use. The container 28 should be secured during shipment and storage of the test kit 10 in order to preserve the condition and contents of the test filter 20 before and after testing. When the test device T is in use, the test device T is removed from the container 28. The container 28 can be of any type as long as the test filter 20 fits inside the container 28 when not in use. One example of the container 28 is depicted in FIG. 1, which shows a plastic bag with a self sealing connection. Other examples of the container 28 are a molded plastic container that seals or a sealable cardboard box.

In general, the test kit 10 is used by a homeowner who has purchased pre-assembled test kit 10. The test kit 10 is sold in a package 12 that includes a test device T formed by a test filter 20, a support 18 and a filter backing pad 22. The test kit 10 also includes instructions 14 for use and an order form 16 to be filled out when submitting the test kit 10 for analysis.

Second, the homeowner takes the purchased test kit 10 home and removes the test kit 10 from the packaging 12. The test device T is placed on a device that produces air circulation, such as a heating and ventilation system, a fan or a vacuum cleaner.

Third, the air circulation device is then operated for a recommended length of time that is specified in the test kit instructions 14. The operation of the air circulation device will cause air to flow through the test filter 20. As air moves through the test filter 20, the test filter 20 will capture and retain air contaminants.

Fourth, after the specified period of operation, the homeowner removes the test device T from the air circulation device.

Fifth, the test device T is then repackaged and sent to a test facility with a request for analysis. Along with the test device T, the order form 16 provided with the test kit 10 is filled out and sent to the test facility to assist the test facility in interpreting the contaminants collected by the test device T.

Sixth, the test facility performs an analysis on the test filter 20 and provides an air quality report to the homeowner.

Figure 2:
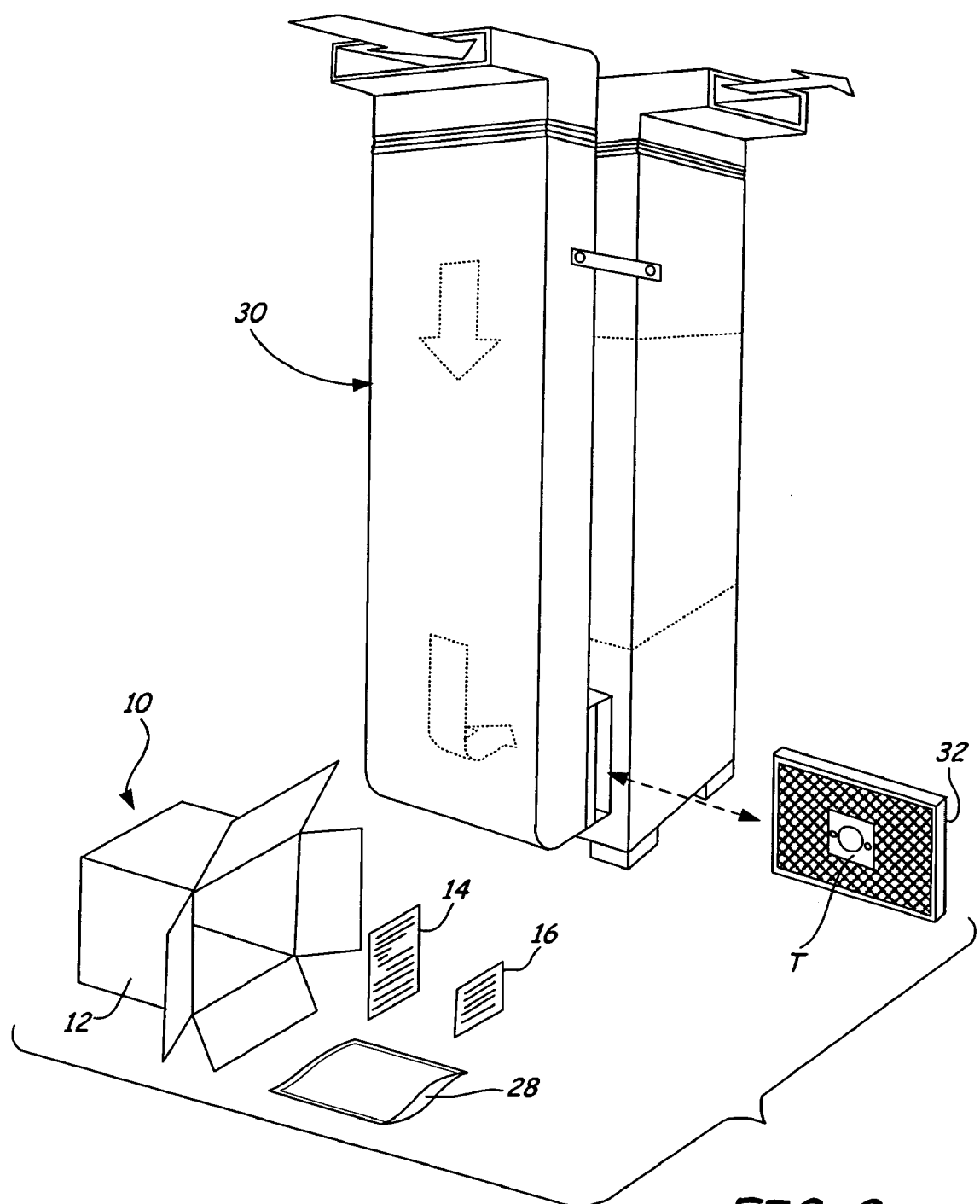
FIG. 2 is a perspective view of a standard heating and ventilation system along with the test kit.

FIG. 2 illustrates a typical home heating and ventilation system 30 along with the test kit 10. To use the test kit 10 with the home heating and ventilation system 30, first the user removes the existing particulate filter 32 from the heating and ventilation system 30.

Second, the test device T is then removed from the container 28 while making sure not to touch the test filter 20. With the test filter 20 facing towards the air-flow, the test device T is placed in the center of the existing particulate filter 32.

Third, the test device T is fastened to the existing particulate filter 32 by pushing the pair of pins 26 through the pin openings 24 and all the way through the existing particulate filter 32.

Fourth, the fastened test device T and particulate filter 32 are inserted into the existing filter housing 34 facing towards the air-flow.

Fifth, a blower of the heating and ventilation system 30 is operated. The blower should run continually for a minimum of four hours up to a maximum of 16 hours ("sampling period"). The blower will cause air to flow through the test filter 20. As air moves through the test filter 20, the test filter 20 will capture and retain air contaminates.

Sixth, the start time of the sampling period is recorded on the order form 16 as well as that the heating and ventilation system testing method was used.

Seventh, after the sampling period is completed, the test device T and the existing particulate filter 32 are removed from the heating and ventilation system 30.

Eighth, the test device T is removed from the existing particulate filter 32 while taking care not to touch the test filter 20.

Ninth, the test device T is placed back into the container 28 for mailing.

Tenth, the finish time of the sampling period is recorded on the order form 16 as well as any remaining information on the order form 16.

Eleventh, the test device T and the order form 16 are mailed together to the testing facility for analysis. The testing facility performs an analysis on the test filter 20 and provides an air quality report to the user. Using the heating and ventilation system 30 for testing is the preferred and most accurate method to measure indoor air quality.

Figure 3:
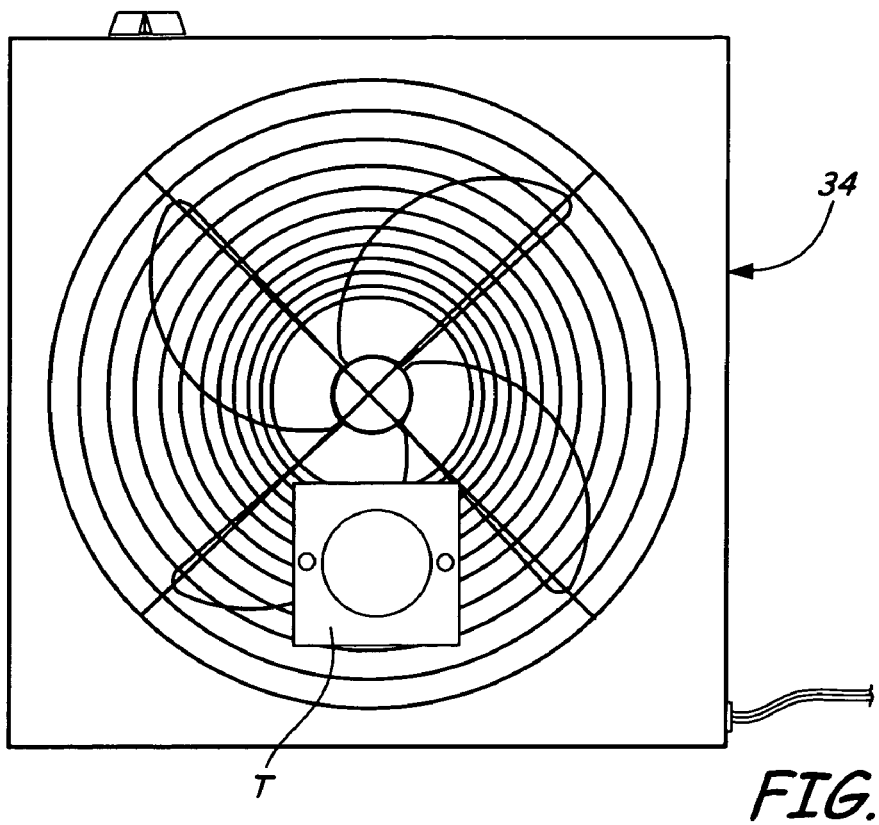
FIG. 3 is a perspective view of a standard box fan along with the test device.

FIG. 3 is a perspective view of a standard box fan 34 along with the test device T. Although a box fan 34 is shown in FIG. 2, any other type of fan may be used with the test kit 10. To use the test device T with the box fan 34, the fan 34 is first placed in a central location within a room to be tested.

Second, the fan 34 is turned on to operate on the high setting.

Third, the test device T is removed from the container 28 while making sure not to touch the test filter 20.

Fourth, the test device T is placed on the inlet side of the fan 34 halfway up from the bottom of the fan 34 and two inches in from the outer edge of the fan 34. The suction from the fan 34 will keep the test filter 20 in place, however, the support 18 should be taped in place to prevent movement.

Fifth, the fan 34 continues to operate on the high setting for a minimum of 24 hours up to a maximum of 72 hours ("sampling period"). The fan 34 will cause air to flow through the test filter 20. As air moves through the test filter 20, the test filter 20 will capture and retain air contaminates.

Sixth, the start time of the sampling period is recorded on the order form 16 as well as that the fan testing method was used.

Seventh, after the specified period of operation, the test device T is removed from the fan 34 while taking care not to touch the test filter 20.

Eighth, the test device T is then repackaged in the container 28 for mailing.

Ninth, the finish time of the sampling period is recorded on the order form 16 as well as any remaining information on the order form 16.

Tenth, the test device T and the order form 16 are mailed together to the testing facility for analysis. The testing facility performs an analysis on the test filter 20 and provides an air quality report to the user. Using the box fan 34 testing method allows a homeowner to test for air contaminates in a particular room.

Figure 4:
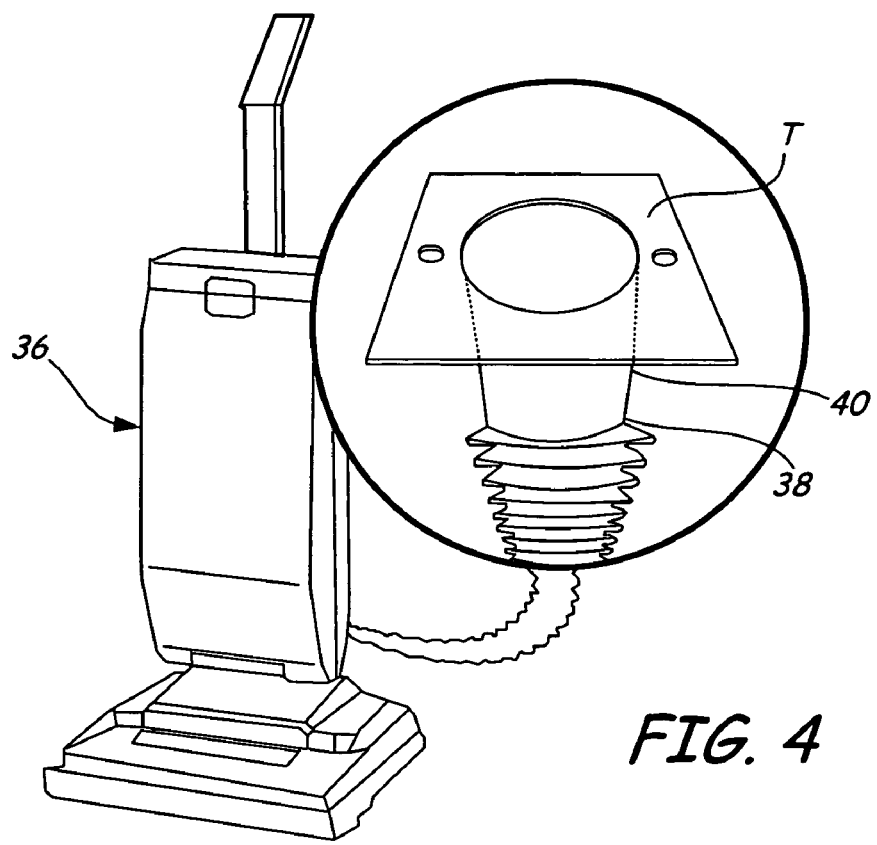
FIG. 4 is a perspective view of a standard vacuum cleaner along with the test device.

FIG. 4 is a perspective view of a standard vacuum cleaner 36 along with the test device T. To use the test device T with the vacuum cleaner 36, first the vacuum cleaner 36 is placed in a central location within in a room to be tested. Second, an attachment hose 38 without any attachments is connected to the vacuum cleaner 36. The end 40 of the attachment hose 38 should be placed between one to four feet off of the floor.

Third, the vacuum cleaner 36 is turned on.

Fourth, the test device T is removed from the container 28 and is placed on the end 40 of the attachment hose 38. The test filter 20 is placed in the center of the end 40 of the attachment hose 38. The suction from the vacuum cleaner 36 will keep the test filter 20 in place.

Fifth, the vacuum cleaner 36 continues to operate for a minimum of 3 minutes up to a maximum of 6 minutes ("sampling period"). The vacuum cleaner 36 will cause air to flow through the test filter 20. As air moves through the test filter 20, the test filter 20 will capture and retain air contaminates.

Sixth, the start time of the sampling period is recorded as well as that the vacuum cleaner testing method was used.

Seventh, after the specified sampling period, the test device T is removed from the vacuum cleaner 36 while taking care not to touch the test filter 20.

Eighth, the test device T is then repackaged in the container 28 for mailing.

Ninth, the finish time of the sampling period is recorded on the order form 16 as well as any remaining information on the order form 16.

Tenth, the test device T and the order form 16 are mailed together to the testing facility for analysis. The testing facility performs an analysis on the test filter 20 and provides an air quality report to the user.

Using the vacuum cleaner 36 testing method allows a homeowner to test for air contaminates in a particular room or to sample the exhaust air from a vacuum cleaner 36. Additionally, using a vacuum cleaner 36 allows a shorter sampling period. However, vacuum cleaners 36 are known for expelling microscopic contaminates into the air.

Although the present invention has been described with reference to preferred embodiments, workers skilled in the art will recognize that changes may be made in form and detail without departing from the spirit and scope of the invention.

The invention claimed is:

1. A method for testing air quality contaminants, the method comprising:
   providing a test kit that includes a test filter and a support;
   removing the test filter and the support from a protective container;
   placing the test filter and the support on a device that produces air circulation, and wherein the test filter and support form a thin and substantially flat card sized to fit without folding in an envelope substantially no larger than letter size;
   causing air to flow through the test filter by operating the device that produces air circulation for a predetermined length of time;
   removing the test filter and the support from the device that produces air circulation;
   replacing the test filter and the support in the protective container;
   placing the protective container with the test filter and the support in the envelope;
   sending the envelope to a testing facility for analysis of the test filter; and
   receiving an air quality report from the testing facility.

2. A method as in claim 1, wherein the device that produces air circulation is selected from the group consisting of a heating and ventilation system, a fan and a vacuum cleaner.

3. A method as in claim 1, including the steps of:
   recording a start time of blower operation;
   recording a type of device used to produce air circulation;
   recording a finish time of blower operation; and
   selecting tests to be performed on the test filter.

4. The method of claim 1, wherein the step of placing the test filter and the support on the device that produces air circulation includes aligning the test filter with an inlet end of a vacuum cleaner, wherein the step of causing air to flow through the test filter by operating the device that produces air circulation for a predetermined length of time includes running the vacuum cleaner for a predetermined length of time; and wherein the step of removing the test filter and the support from the device that produces air circulation includes removing the test device from the vacuum cleaner.

5. The method of claim 4 and further comprising the step of hooking up an attachment hose to the vacuum cleaner without an attachment end.

6. The method of claim 5 and further comprising the step of positioning the attachment hose between one to four feet off of the floor.

7. The method of claim 4, wherein the test device remains supported at the inlet end of the vacuum cleaner due to suction of the vacuum cleaner.

8. The method of claim 4, wherein the vacuum cleaner runs for a minimum of three minutes to a maximum of six minutes.

9. The method of claim 4 and further comprising the steps of:
recording a start time of running the vacuum cleaner;
recording a finish time of running the vacuum cleaner; and
selecting tests to be performed on the test filter.

10. The method of claim 1 and further comprising:
operating a fan on a highest setting;
wherein the step of placing the test filter and the support on the device that produces air circulation includes placing the test filter and the support on an inlet side of the fan;
wherein the step of causing air to flow through the test filter by operating the device that produces air circulation for a predetermined length of time includes running the fan for a predetermined length of time with the test filter and the support on the inlet side of the fan; and
wherein the step of removing the test filter and the support from the device that produces air circulation includes removing the test device from the fan.

11. The method of claim 10, wherein the step of placing the support and the test filter on the inlet side of the fan includes placing a perimeter of the support halfway up from a side of the fan and two inches in from an outer edge of the fan.

12. The method of claim 10, wherein the fan is a box fan.

13. The method of claim 10 and further including the step of:
taping the support to the fan to prevent movement.

14. The method of claim 10, wherein the test filter and the support remain in place due to suction of the fan.

15. The method of claim 10 and further comprising the steps of:
recording a start time of running the fan;
recording a finish time of running the fan; and
selecting tests to be performed on the test filter.

16. The method of claim 10, wherein the fan runs for a minimum of 24 hours to a maximum of 72 hours.

17. The method of claim 1 and further comprising the steps of:
removing a particulate filter from a filter housing of a heating and ventilation system;
placing the support and the test filter in the center of the particulate filter on a side towards air flow;
fastening the support and the test filter to the particulate filter;
inserting the fastened support, test filter and particulate filter into the filter housing;
wherein the step of placing the test filter and the support on the device that produces air circulation includes blowing air through the test filter by operating a blower of the heating and ventilation system;
wherein the step of removing the test filter and the support from the device that produces air circulation includes removing the support the test filter and the particulate filter from the heating and ventilation system; and
removing the support and the test filter from the particulate filter.

18. The method of claim 17, wherein fastening the support and the test filter to the particulate filter includes fastening at least the support to the particulate filter with a plurality of pins.

19. The method of claim 17, wherein the blower is operated to blow air through the test filter for a minimum of four hours up to a maximum of 16 hours.

20. The method of claim 19 and further comprising:
recording a start time of blower operation;
recording a finish time of blower operation; and
selecting tests to be performed on the test filter.

* * * * *